(12) United States Patent
Jennings

(10) Patent No.: US 7,534,158 B2
(45) Date of Patent: May 19, 2009

(54) MATERNAL EXPANDABLE PROTECTOR

(76) Inventor: Jennifer Jennings, 3537 Baker Rd., Orchard Park, NY (US) 14127

(*) Notice: Subject to any disclaimer, the term of this patent is extended or adjusted under 35 U.S.C. 154(b) by 760 days.

(21) Appl. No.: 11/015,128

(22) Filed: Dec. 17, 2004

(65) Prior Publication Data

US 2005/0136798 A1 Jun. 23, 2005

Related U.S. Application Data

(60) Provisional application No. 60/532,005, filed on Dec. 22, 2003.

(51) Int. Cl.
*A41C 1/08* (2006.01)

(52) U.S. Cl. .................. 450/155; 450/134; 450/104; 450/106

(58) Field of Classification Search ........... 450/155, 450/134, 106, 104; 602/19; 128/99.1, 100.1, 128/101.1
See application file for complete search history.

(56) References Cited

U.S. PATENT DOCUMENTS

| 1,110,226 | A | * | 9/1914 | Payne | 450/106 |
| 1,250,048 | A | * | 12/1917 | Temple | 450/128 |
| 3,491,764 | A | * | 1/1970 | Simonsen | 450/104 |
| 4,108,149 | A | * | 8/1978 | Castiglia | 450/155 |
| 4,195,640 | A | * | 4/1980 | Castiglia | 450/155 |
| 5,492,496 | A | * | 2/1996 | Walker | 450/155 |
| 6,071,175 | A | * | 6/2000 | Working, III | 450/155 |
| 6,592,428 | B2 | * | 7/2003 | Smith | 450/134 |

* cited by examiner

*Primary Examiner*—Gloria Hale
(74) *Attorney, Agent, or Firm*—Roach Brown McCarthy & Gruber, P.C.; Kevin D. McCarthy

(57) ABSTRACT

The present invention is directed to a maternal protector. The maternal protector has at least a flexible protection device and a pocket in a pocket positioning material. The pocket receives a portion of the flexible protection device. The pocket positioning material positions the pocket over a mother to allow the protection device to be positioned over at least a portion of the mother's uterus.

13 Claims, 3 Drawing Sheets

MATERNAL EXPANDABLE PROTECTOR

CLAIM OF PRIORITY

This application claims priority to U.S. provisional patent application Ser. No. 60/532,005, filed on Dec. 22, 2003.

FIELD OF THE INVENTION

The present invention is directed to a device that has a chance to decrease injuries to a fetus.

BACKGROUND OF THE INVENTION

There are numerous devices to assist a pregnant mother during a pregnancy. One of those devices is a back support 10. An example of a back support device 10 is illustrated in FIG. 1, and can be purchased from Scott Specialties, Inc. of Belleville, Kans. You can view the product at allegromedical.com/scott-specialties.htm/. The back support device 10 has a stretchable back unit 12 and an interconnecting comfortable front unit 14.

The front unit 14 is made of a soft and loop-like material 16 and an adjustable strap 17. The soft and loop-like material is designed to overlay, and not penetrate into, the uterus area of the mother. The adjustable strap 17 is interconnected to material 16 and at the distal end of the strap 17 is a hook-like connector. Once the material 16 is properly positioned about the uterus, the strap 17 is wrapped around the back of the mother and interconnected to the loop-like material 16 until the front unit 14 is comfortably positioned on the mother.

The stretchable back unit 12 works in conjunction with the front unit 14. The back unit 12 does not have to be used in association with the front unit 14 but if back issues exist, it could be used by the mother. The back unit 12, as used in the prior art, has the stretchable material 20 and two hook-like extensions 22 a,b at the terminal ends of the stretchable material 20. The extensions 22 a,b interconnect with the loop-like material 16 until the back unit 12 is properly positioned on the mother.

The support device 10 as presently sold does not in the applicant's opinion provide adequate protection to the pregnant mother. The applicant has prepared some research on the types of conditions that pregnant mother's experience.

There is research that indicates that pregnant mothers are subject to many physical hazards and trauma that other non-pregnant females experience. Those hazards and trauma are caused for various reasons. Some of those reasons include and are not limited to motor vehicle accidents, falls/assaults, domestic violence, occupational safety, and exercise/athletics/sports.

Those hazards and trauma are a result of the mother's condition changing and her environment. As the mother's pregnancy progresses, her equilibrium and/or balance may change due to the position of the fetus and/or the temporary weight gain. These changes could make it difficult for the mother to perform her job, exercise, drive, and stand. As for environmental changes, it has been documented that some partners of the pregnant mother become more abusive. Such abusive behavior is unacceptable domestic abuse, but it sometimes occurs.

What to do to decrease the effect on the fetus during such hazards and trauma? The present invention solves this problem.

SUMMARY OF THE INVENTION

The present invention is directed to a maternal protector. The maternal protector has at least a flexible protection device and a pocket in a pocket positioning material. The pocket receives a portion of the flexible protection device. The pocket positioning material positions the pocket over a mother to allow the protection device to be positioned over at least a portion of the mother's uterus.

BRIEF DESCRIPTION OF THE FIGURES

FIG. 2 illustrates one embodiment of the present invention wherein

DETAILED DESCRIPTION OF THE PRESENT INVENTION

In one embodiment of the present invention, the back support 10a is modified to obtain the desired protection for a pregnant mother.

Figure 1:
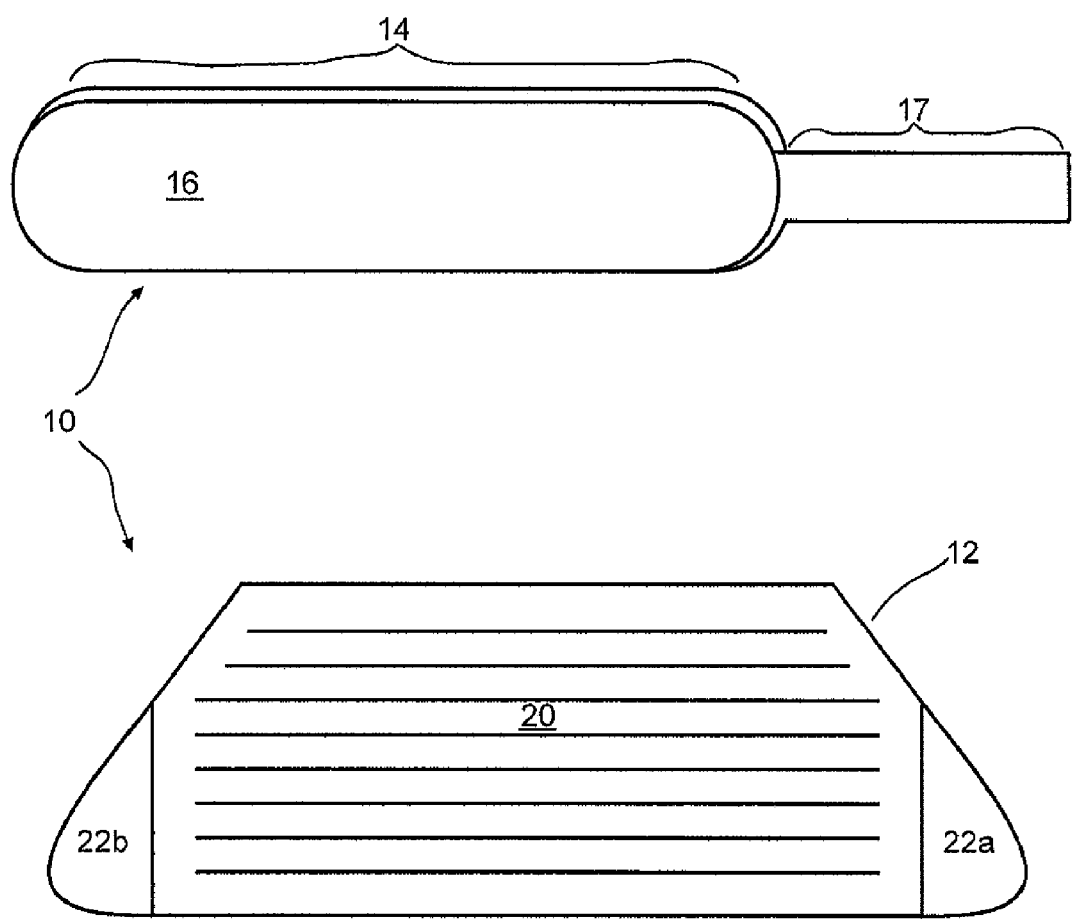
FIG. 1 illustrates the prior art illustrating a front unit 14 and a strap 17 and back unit 12.
Figure 2A:
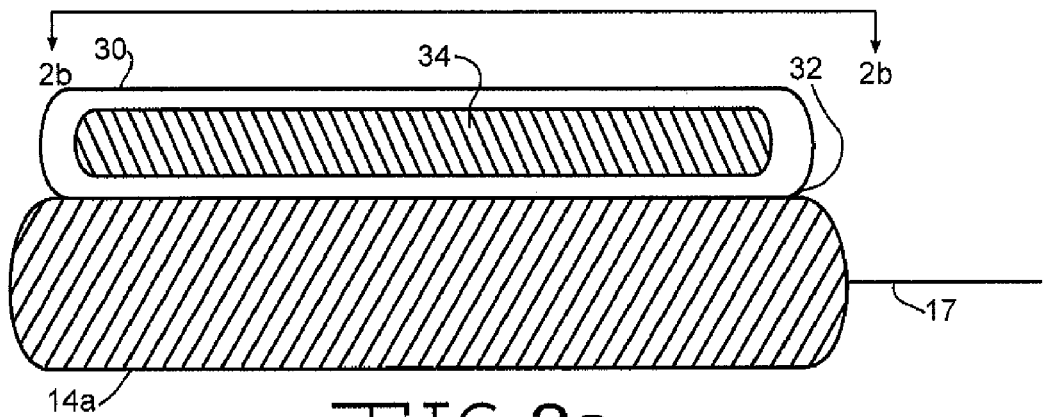
FIG. 2a illustrates how the protective device is positioned in a pocket of the front unit 14.
Figure 2B:
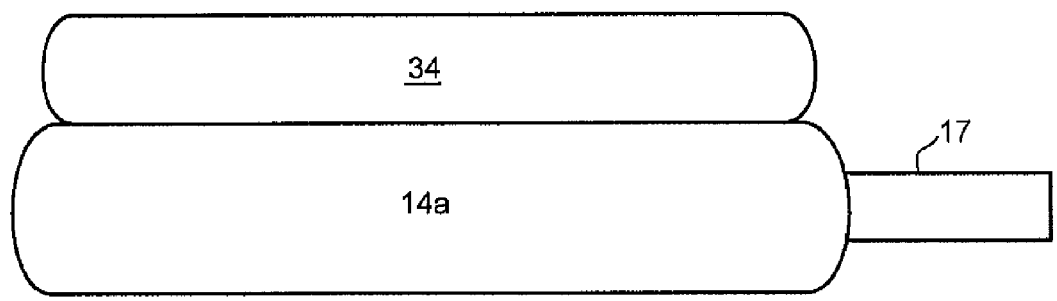
FIG. 2b illustrates a view of FIG. 2a taken along the lines 2b-2b.
Figures 2C, 2D:
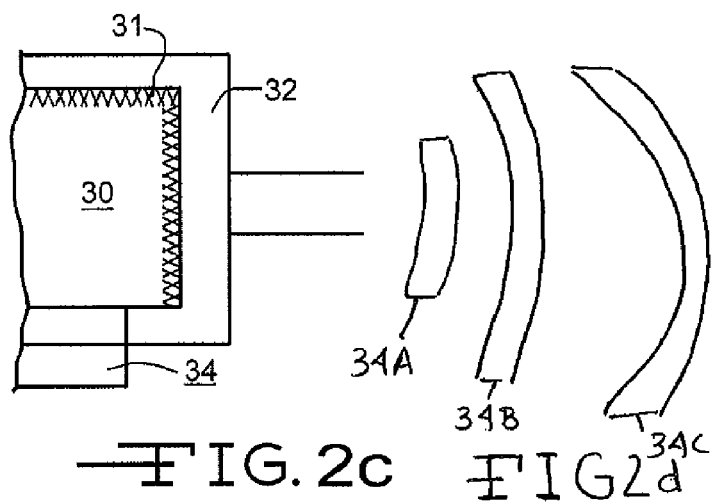
FIG. 2c illustrates an enlarged view of FIG. 2a taken along the lines 2c-2c.
FIG. 2d illustrates different size protective devices that fit into the pocket of the front unit 14
Figure 3:
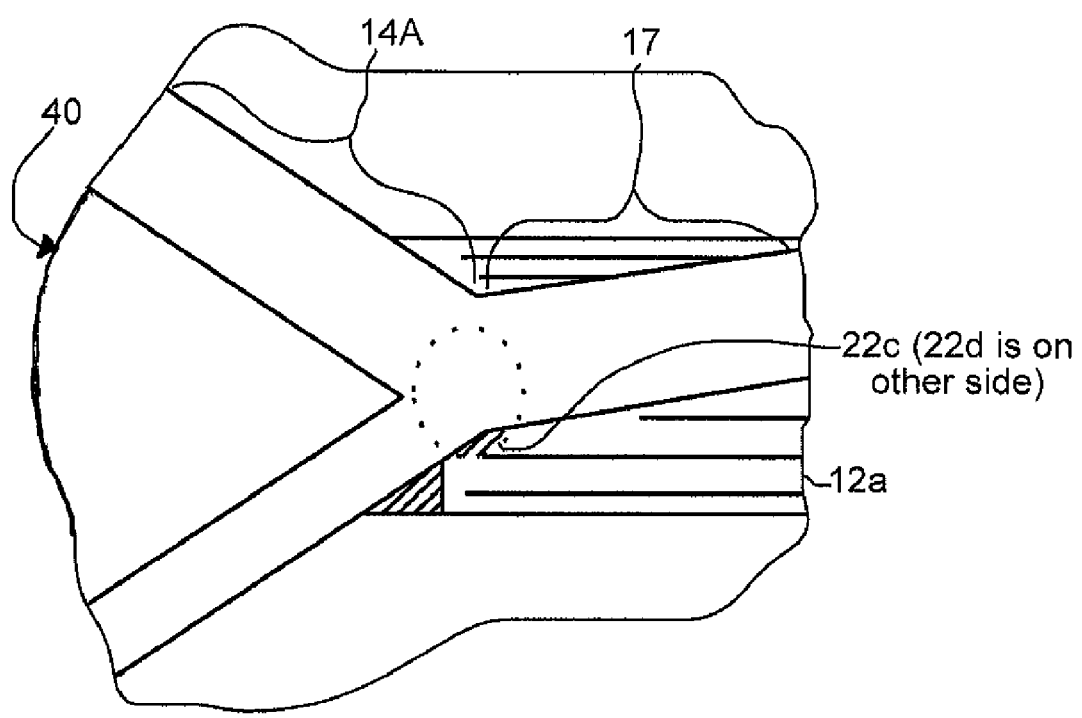
FIG. 3 illustrates an alternative embodiment of the present invention as positioned on a pregnant female wherein the back unit 12 is positioned on the female's back area, the strap 17 is positioned over the back unit 12 and the front unit 12 is positioned on the frontal exterior surface of the female's skin which is were the uterus which carries a fetus normally expands.

In a first embodiment of the present invention, the front unit 14a is modified by adding a pocket 30 as illustrated in FIGS. 2a and 2b. The pocket 30 is positioned on the surface 32 of the front unit 14a that faces the mother's skin, as illustrated in FIG. 3. The pocket 30 is attached to surface 32 by any conventional fastening device 31 to form a conventional pocket, as illustrated in FIGS. 2a, 2b and 2c. These conventional fastening devices 31 include and are not limited to stitching, adhesives, rivets, fasteners such as buttons and apertures, snap-ons, hook and loop designs; and combinations thereof.

The pocket 30 receives a flexible protector device 34, as illustrated in FIGS. 2a, 2b, and 2c. The protector device 34 should be flexible to adapt and conform to the various shapes of a mother's bulging uterus 40, as illustrated in FIG. 3. Examples of the flexible device 34 include and are not limited to polymeric materials, a gelastic material, and/or metallic materials. In addition, the flexible protective devices can also contain fluids like water which could provide further protective qualities. Since the material list is endless, the limitations to the materials used for the device 34 are limited only in the weight of the material and the flexibility of the material to at least attempt to conform to the shape of the mother.

There can various sizes of the protective devices 34. There are small sizes 34a, medium sizes 34b, large sizes 34c as illustrated at FIG. 2d, and anything in between. Which size is used is dependent on the mother and her comfort level. Moreover, the mother can interchange the various sizes of the protective devices during the term of the pregnancy.

For large sizes, applicant recommends a modified stretchable back unit 12a be used, as illustrated in FIG. 3. The modified stretchable back unit 12a is modified by adding additional conventional fastening devices 22 c,d. These additional conventional fastening devices are designed to interconnect with a corresponding fastening device positioned on the large size of the protective device. The large size of the protective device, it has been determined, needs the additional fastening devices to secure the protective device to the mother.

In another embodiment, the pocket 30 can be positioned within the mother's undergarments positioned around her uterus. In another embodiment, the pocket 30 can be positioned within the mother's clothing—shirts, dresses, skirts, and/or pants. The only requirement of the preferred embodiment and these alternative embodiments is that the pocket positioning material ensures that the pocket that receives at least a portion of the protection device is positioned so the protection device is positioned over at least a portion of the mother's uterus.

By no means does this maternal protection device prevent injuries to the mother and the fetus. Instead, this device 10 is designed to merely decrease the chance of any such injuries to the mother and the fetus. It is equivalent to hockey equipment; it can decrease the chances of a user obtaining some injuries but not all injuries.

Many modifications and variations of our invention will be evident to those skilled in the art. It is understood that such variations may deviate from specific teachings of this description without departing from the essence of the invention, which is expressed in the following claims.

I claim:

1. A maternal protector comprising:
   a back support device having (a) a front unit positioned over a mother's frontal exterior skin surface that overlays the mother's uterus area; (b) a strap that extends from the front unit toward the mother's back and covers a portion of the mother's back to secure the front unit over the frontal exterior skin surface that overlay's the mother's uterus area, and (c) a back unit that supports a portion of the mother's back;
   a first flexible protection device used during an early stage of gestation during the mother's pregnancy and a second flexible protection device, larger than the first flexible protection device, used in a latter stage of gestation during the mother's pregnancy;
   a pocket on the front unit;
   the pocket has a surface that contacts the mother's frontal exterior skin surface that overlays the mother's uterus area and is positioned over at least a portion of the frontal exterior skin surface that overlays the mother's uterus area, the pocket receives the first flexible protection device which is interchangeable with the second flexible protection device during the latter stage of gestation during the mother's pregnancy to provide the appropriate protection to the mother and the fetus.

2. The maternal protector of claim 1 wherein the pocket is secured to the front unit by fastening devices.

3. The maternal protector of claim 2 wherein the fastening devices are selected from the group consisting of stitching, adhesives, rivets, fasteners such as buttons and apertures, snap-ons, a hook and loop fastener; and combinations thereof.

4. The maternal protector of claim 1 wherein the back support device is clothing material selected from the group consisting of undergarments, shirts, dresses, skirts, pants.

5. The maternal protector of claim 1 wherein the back unit is a stretchable back unit.

6. The maternal protector of claim 5 wherein the stretchable back unit has at least two fastening devices to interconnect with the front unit.

7. The maternal protector of claim 1 wherein the first flexible protector device comprises a polymeric material.

8. The maternal protector of claim 1 wherein the first flexible protector device comprises metal.

9. The maternal protector of claim 1 wherein the first flexible protector device comprises metal and polymeric material.

10. The maternal protector of claim 1 wherein the first flexible protector device comprises a gelastic material.

11. The maternal protector of claim 1 wherein the first flexible protector device is selected from the group consisting of metal, polymeric material, gelastic material, fluid, or combinations thereof; and the second flexible protector device is selected from the group consisting of metal, polymeric material, gelastic material, fluid, or combinations thereof.

12. A maternal protector comprising:
    a maternal garment having (a) a front unit positioned over a mother's frontal exterior skin surface that overlays the mother's uterus area, and (b) a strap that extends from the front unit toward the mother's back and covers a portion of the mother's back to secure the front unit over the frontal exterior skin surface that overlay's the mother's uterus area;
    a first flexible protection device;
    a pocket on the front unit and is positioned over at least a portion of the frontal exterior skin surface that overlays the mother's uterus area, the pocket receives the first flexible protection device which can be interchanged with a second flexible protection device which is larger than the first flexible protection device.

13. The maternal protector of claim 12 wherein the first flexible protector device is selected from the group consisting of metal, polymeric material, gelastic material, fluid, or combinations thereof; and the second flexible protector device is selected from the group consisting of metal, polymeric material, gelastic material, fluid, or combinations thereof.

* * * * *